(12) United States Patent
Schuele

(10) Patent No.: US 8,844,536 B1
(45) Date of Patent: Sep. 30, 2014

(54) LOCKING APPARATUS FOR A HEAD FIXATION DEVICE

(75) Inventor: Matthias E. Schuele, Freiburg (DE)

(73) Assignee: pro med instruments GmbH, Freiburg (DE)

( * ) Notice: Subject to any disclaimer, the term of this patent is extended or adjusted under 35 U.S.C. 154(b) by 223 days.

(21) Appl. No.: 13/216,659

(22) Filed: Aug. 24, 2011

Related U.S. Application Data

(60) Provisional application No. 61/376,540, filed on Aug. 24, 2010.

(51) Int. Cl.

| | | |
|---|---|---|
| *A47B 7/00* | (2006.01) |
| *A47C 20/00* | (2006.01) |
| *A61G 15/00* | (2006.01) |
| *A61F 5/37* | (2006.01) |
| *A61B 19/00* | (2006.01) |
| *F16B 7/10* | (2006.01) |
| *F16D 1/12* | (2006.01) |
| *F16C 11/00* | (2006.01) |
| *F16D 3/00* | (2006.01) |
| *A61F 5/00* | (2006.01) |
| *A61B 17/00* | (2006.01) |
| *A61B 17/56* | (2006.01) |
| *A61F 5/04* | (2006.01) |

(52) U.S. Cl.
USPC ............ 128/845; 5/621; 5/622; 5/636; 5/637; 5/640; 5/643; 128/846; 128/869; 403/83; 403/84; 403/86; 403/87; 602/17; 602/32; 602/33; 602/35; 602/37; 606/1; 606/53; 606/54; 606/59; 606/130

(58) Field of Classification Search
USPC ............ 5/622, 637, 640, 643, 621; 128/846, 128/869; 602/17, 32, 33, 35, 36, 37; 600/233, 234, 229, 417, 429; 606/1, 606/54, 59, 130, 53; 403/87, 110, 196, 234, 403/240, 256, 338, 83
See application file for complete search history.

(56) References Cited

U.S. PATENT DOCUMENTS

| | | |
|---|---|---|
| 1,839,726 A | 1/1932 | Arnold |
| 2,586,488 A | 2/1952 | Smith |
| (Continued) | | |

FOREIGN PATENT DOCUMENTS

| | | |
|---|---|---|
| EP | 1 026 513 | 8/2000 |
| EP | 2 014 251 | 1/2009 |
| (Continued) | | |

OTHER PUBLICATIONS

Accessories, Officine Sordina S.p.A.

(Continued)

*Primary Examiner* — Michael Brown
*Assistant Examiner* — Brandon L Jackson
(74) *Attorney, Agent, or Firm* — Frost Brown Todd LLC

(57) ABSTRACT

A locking apparatus for use with a head fixation device allows for a stabilizing fixture, such as a rocker arm having a pair of skull pins, to be selectively secured so that the stabilizing fixture can be adjustably rotated to a desired position. In some version the locking apparatus includes a connector that is retained within an opening in a portion of the head fixation device. The connector can translate within the opening and is restricted from rotation. The translating of the connector permits the connector to engage an arch member that retains the stabilizing fixture. The engagement of the connector and arch member is accomplished, in some versions, by way of matching axial oriented toothed portions or starburst features. In some versions the teeth on the starburst features include a chamfer surface.

20 Claims, 19 Drawing Sheets

(56) References Cited

U.S. PATENT DOCUMENTS

| | | | |
|---|---|---|---|
| 2,594,086 A | 4/1952 | Smith |
| 3,522,799 A | 8/1970 | Gauthier |
| 3,835,861 A | 9/1974 | Kees et al. |
| 4,312,336 A | 1/1982 | Danieletto et al. |
| 4,392,645 A | 7/1983 | Westphal |
| 4,457,300 A | 7/1984 | Budde |
| 4,539,979 A | 9/1985 | Bremer |
| 4,541,421 A | 9/1985 | Iversen et al. |
| 4,543,947 A | 10/1985 | Blackstone |
| 4,612,930 A | 9/1986 | Bremer |
| 4,615,072 A | 10/1986 | Lautenschlager, Jr. |
| 4,667,660 A | 5/1987 | Eingorn |
| 4,796,846 A | 1/1989 | Meier et al. |
| 4,803,976 A | 2/1989 | Frigg et al. |
| 4,807,605 A | 2/1989 | Mattingly |
| 4,827,926 A | 5/1989 | Carol |
| 4,838,264 A | 6/1989 | Bremer et al. |
| 4,971,037 A | 11/1990 | Pelta |
| 5,042,462 A | 8/1991 | Bremer |
| 5,197,965 A | 3/1993 | Cherry et al. |
| 5,203,765 A | 4/1993 | Friddle, Jr. |
| 5,276,927 A | 1/1994 | Day |
| 5,284,129 A | 2/1994 | Agbodoe et al. |
| 5,300,076 A | 4/1994 | Leriche |
| 5,529,358 A | 6/1996 | Dinkler et al. |
| 5,537,704 A | 7/1996 | Dinkler et al. |
| 5,630,805 A | 5/1997 | Ternamian |
| 5,722,978 A | 3/1998 | Jenkins, Jr. |
| 5,865,780 A | 2/1999 | Tuite |
| 5,891,157 A | 4/1999 | Day et al. |
| 6,110,182 A | 8/2000 | Mowlai-Ashtiani |
| 6,129,729 A | 10/2000 | Snyder |
| 6,198,961 B1 | 3/2001 | Stern et al. |
| 6,306,146 B1 | 10/2001 | Dinkler |
| 6,598,275 B1 | 7/2003 | Kolody et al. |
| 6,659,972 B2 | 12/2003 | Stamper et al. |
| 6,684,428 B2 | 2/2004 | Grotehuis et al. |
| 7,048,735 B2 | 5/2006 | Ferrante et al. |
| 7,232,411 B2 | 6/2007 | Dinkler, II et al. |
| 2001/0029379 A1 | 10/2001 | Grotehuis |
| 2003/0149429 A1 | 8/2003 | Ferrante et al. |
| 2006/0084900 A1 | 4/2006 | Schule |
| 2007/0270801 A1 | 11/2007 | Arn et al. |
| 2008/0251086 A1 | 10/2008 | Dinkler |
| 2009/0264938 A1 | 10/2009 | Bailey et al. |
| 2010/0059064 A1 | 3/2010 | Schule et al. |
| 2010/0217280 A1 | 8/2010 | Schuele et al. |

FOREIGN PATENT DOCUMENTS

| | | |
|---|---|---|
| WO | WO 97/40764 | 4/2001 |
| WO | WO 02/85187 | 10/2002 |

OTHER PUBLICATIONS

Budde Halo Retractor System.
Codman, "Bookwalter Retractor Kit II."
Doro® Skull Pins, pro med instruments, Inc., available at http://www.headrest.de/contentcenter/daten /files/Skull_Pins_Flyer_V01.pdf.
European Search Report dated May 11, 2006 for Application No. EP05292169.
International Preliminary Report on Patentability dated Aug. 30, 2011 for Application No. PCT/IB2010/000513.
International Search Report dated Oct. 18, 2010 for Application No. PCT/IB2010/000513.
Notification Concerning Transmittal of International Preliminary Report on Patentability (Chapter 1 of the Patent Cooperation Treaty) dated Sep. 9, 2011 for Application No. PCT/IB2010/000513.
Partial European Search Report dated Feb. 6, 2006 for Application No. EP 05292169.9.
Screenshots from www.bicakcilar.com, printed Jan. 28, 2005.
Screenshots from www.integra-ls.com, printed Jan. 28, 2005.
Screenshots from www.integra-ls.com, printed Dec. 8, 2005.
Screenshots of Surgical Tables Accessories from www.bicakcilar.com, printed Jan. 28, 2005.
Tuite, Gerald F., M.D. et al., Abstract "Use of an Adjustable Transportable Radiolucent Spinal Immobilization Device in the Comprehensive Management of Cervical Spine Istability," J. of Neurosurgery, vol. 85(6) (Dec. 1996) American Assoc. of Neurosurgeons.

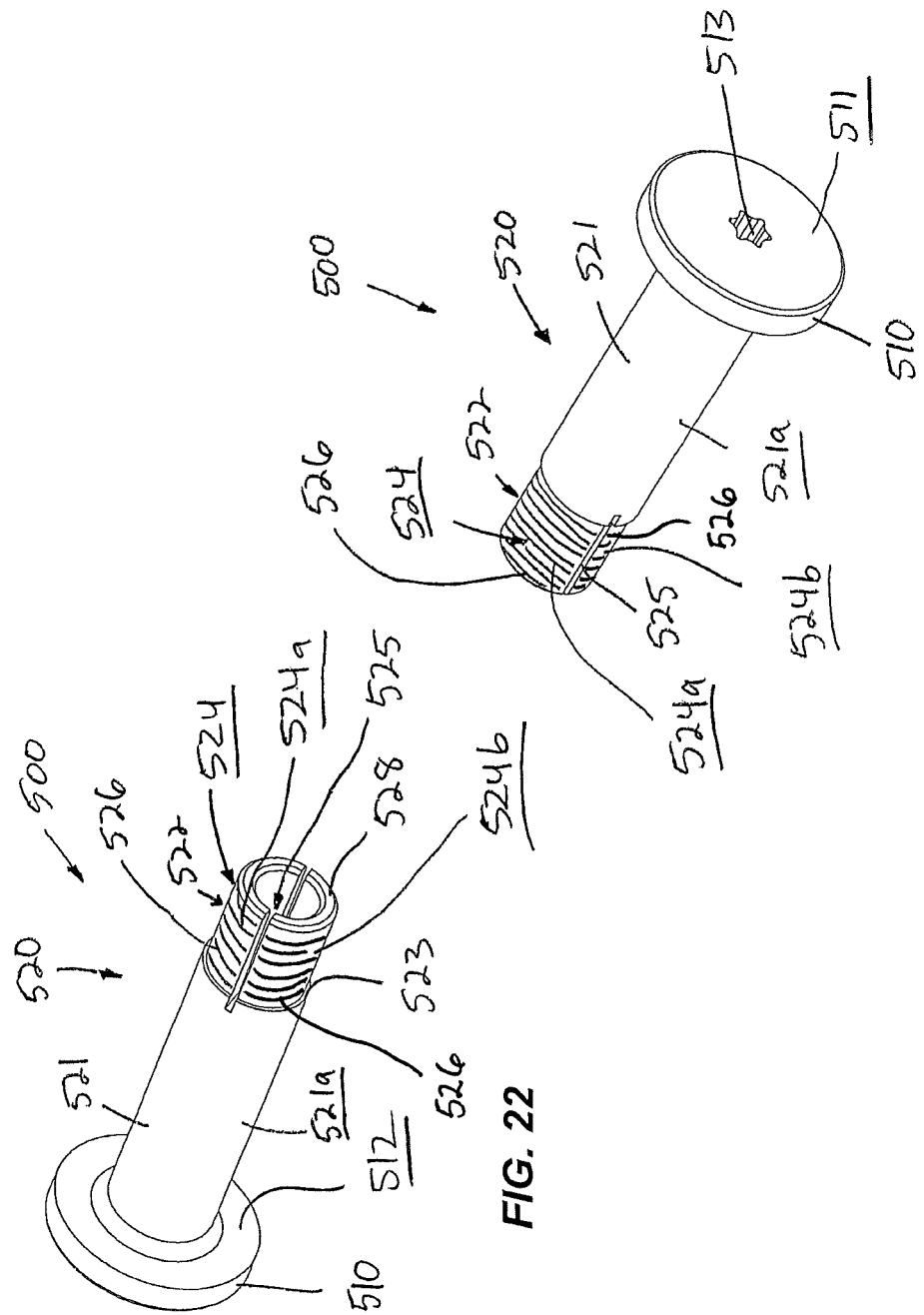

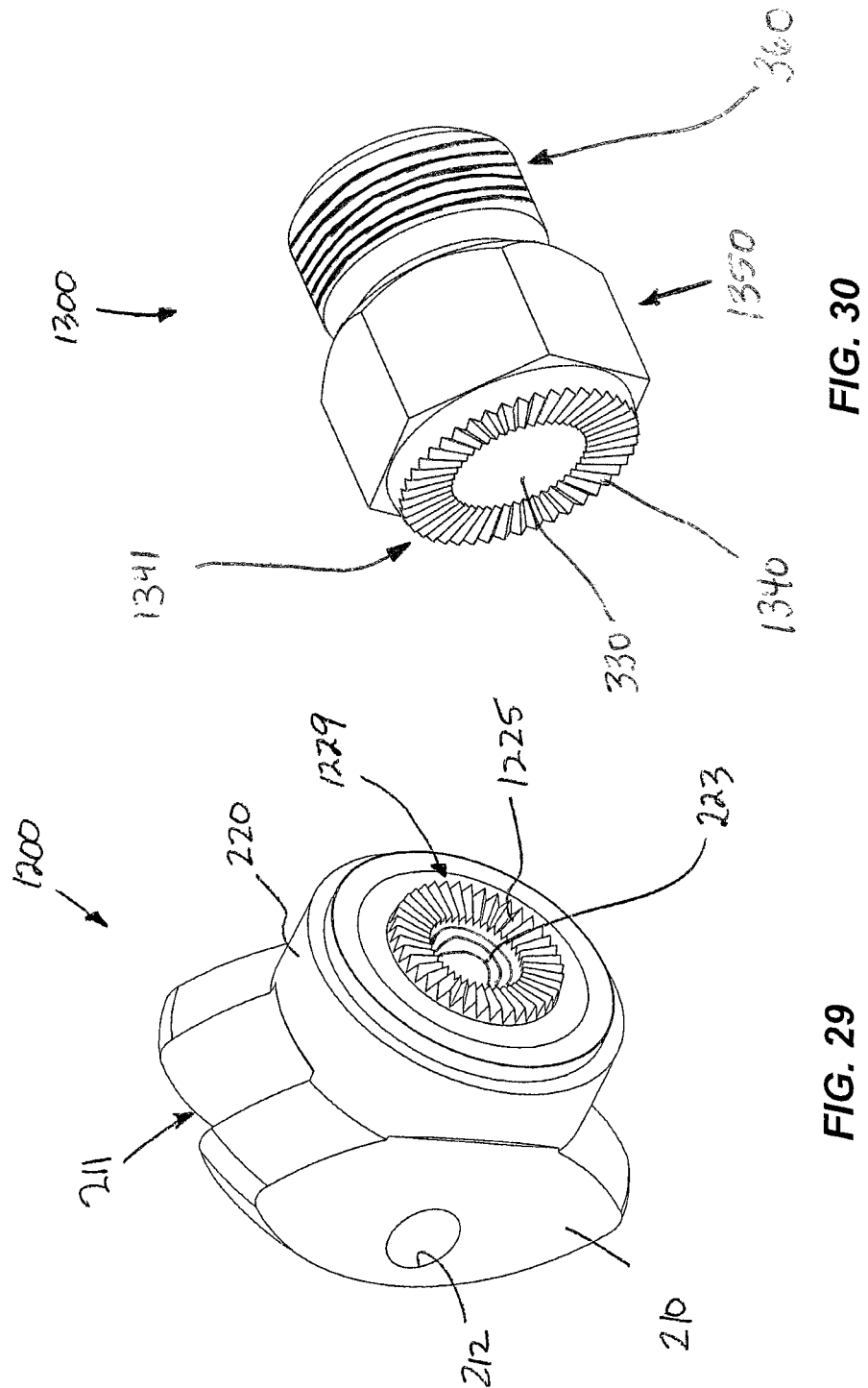

US 8,844,536 B1

LOCKING APPARATUS FOR A HEAD FIXATION DEVICE

PRIORITY

This application claims priority to U.S. Provisional Patent Application Ser. No. 61/376,540, filed Aug. 24, 2010, entitled "Locking Apparatus for a Head Fixation Device," the disclosure of which is incorporated by reference herein.

BACKGROUND

The disclosure provided here relates generally to head fixation devices (hereinafter referred to as "HFDs" or "HFD" in singular), and in particular a locking apparatus for use with a HFD to selectively, yet securely, connect one or more head stabilizing fixtures (e.g., skull pins or gel pads) with a portion of a HFD (e.g., an arm of a skull clamp). While a variety of HFDs and locking apparatuses have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

FIG. 22 depicts a perspective view of the exemplary bolt of FIG. 3.

FIG. 23 depicts another perspective view of the bolt of FIG. 3.

FIG. 29 depicts a perspective view of another exemplary arch member for use with a locking apparatus.

FIG. 30 depicts a perspective view of another exemplary connector for use with a locking apparatus having the arch member of FIG. 29.

Figure 1:
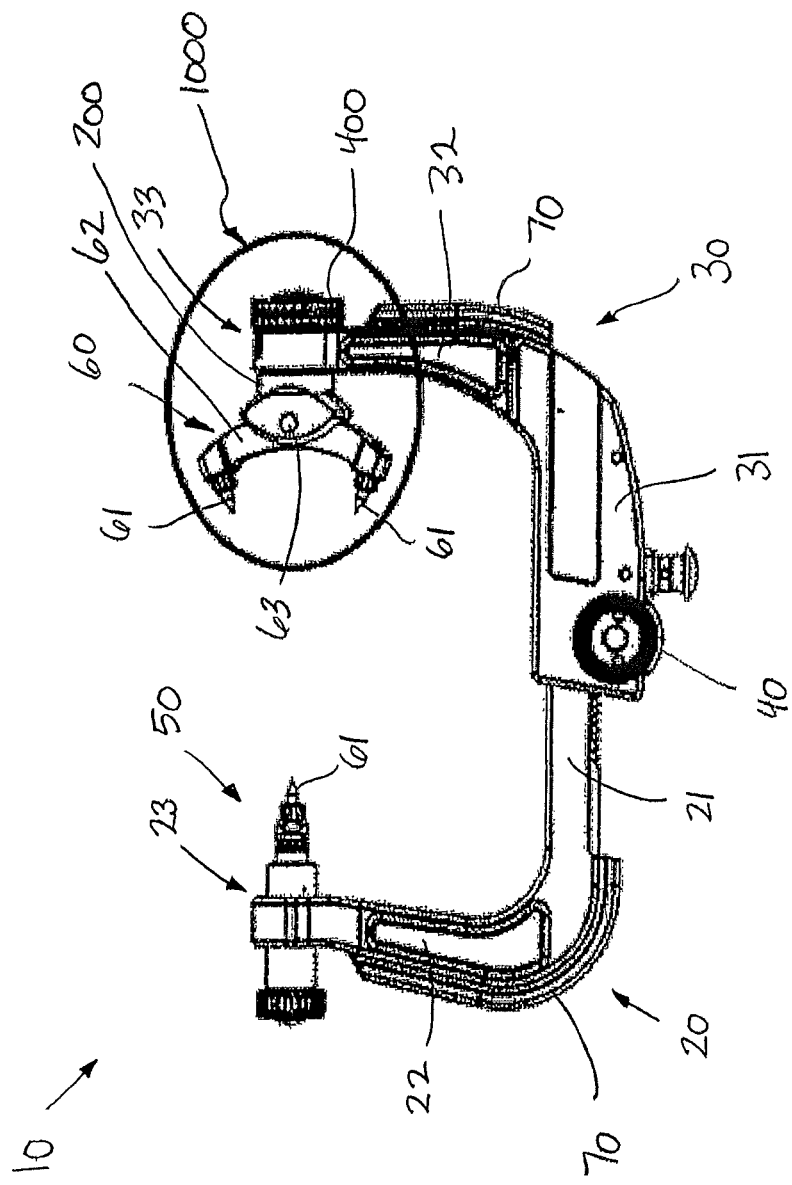
FIG. 1 depicts a front view of an exemplary skull clamp, having an exemplary locking apparatus shown circled.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

I. Exemplary Skull Clamp

FIG. 1 illustrates an exemplary HFD in the form of an exemplary skull clamp (10). Skull clamp (10) comprises a first arm (20), a second arm (30), an interface (40), a single pin fixture (50), a dual pin fixture (60), and rails (70). Skull clamp (10) forms a generally "U" shaped structure with an insert portion (21) of first arm (20) positioned within a receiving portion (31) of second arm (30). First and second arms (20, 30) further comprise generally upright portions (22, 32). In the present example, upright portions (22, 32) include ends (23, 33) respectively, and ends (23, 33) include respective openings (not shown, 34). Openings (not shown, 34) are configured to connect with stabilizing fixtures such as single pin fixture (50) and dual pin fixture (60) respectively. In some versions, stabilizing fixtures can include gel pads instead of or in addition to skull pins. Interface (40) is configured to attach skull clamp (10) to another structure (e.g., an OR table) either directly or indirectly through other intervening structures (e.g., a positioning adapter). In the present example, skull clamp (10) further comprises rails (70) that connect with outwardly facing edges of first and second arms (20, 30); of course rails (70) may be omitted entirely in some versions.

Rails (70) are configured such that various accessories can be connected with skull clamp (10) along rails (70). Other configurations, structures, features, and further description of an exemplary skull clamp such as skull clamp (10) are included in U.S. Pat. No. 7,836,532, entitled METHOD AND APPARATUS FOR ATTACHING ACCESSORIES TO A SURGICAL FIXTURE, issued Nov. 23, 2010, and incorporated by reference herein.

II. Exemplary Locking Apparatus

Figure 2:
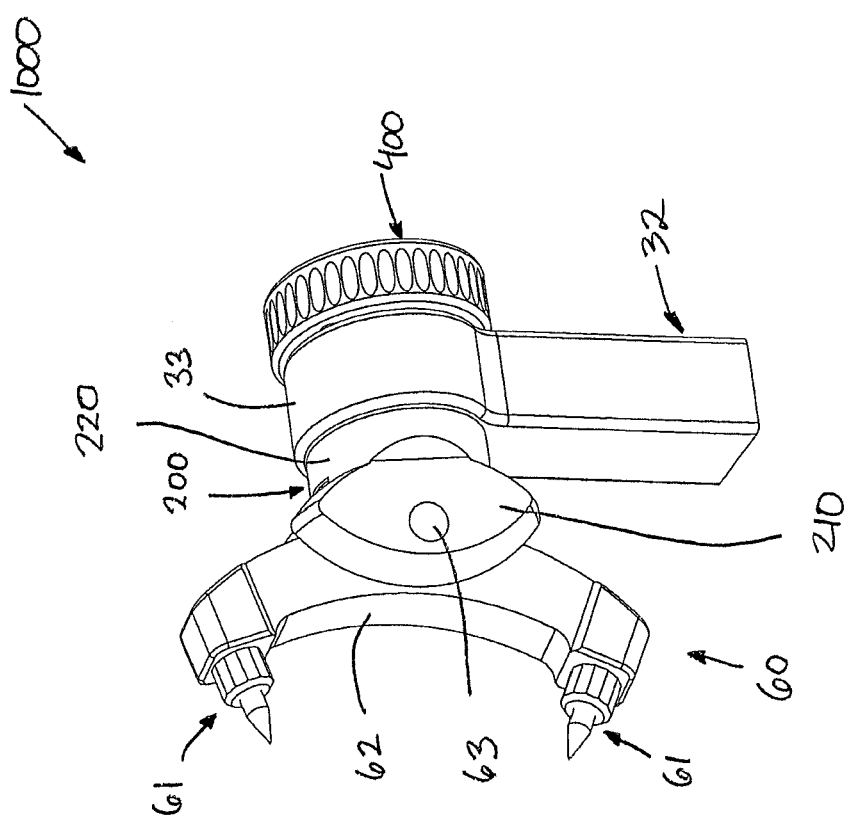
FIG. 2 depicts a perspective view of the locking apparatus of FIG. 1.
Figure 3:
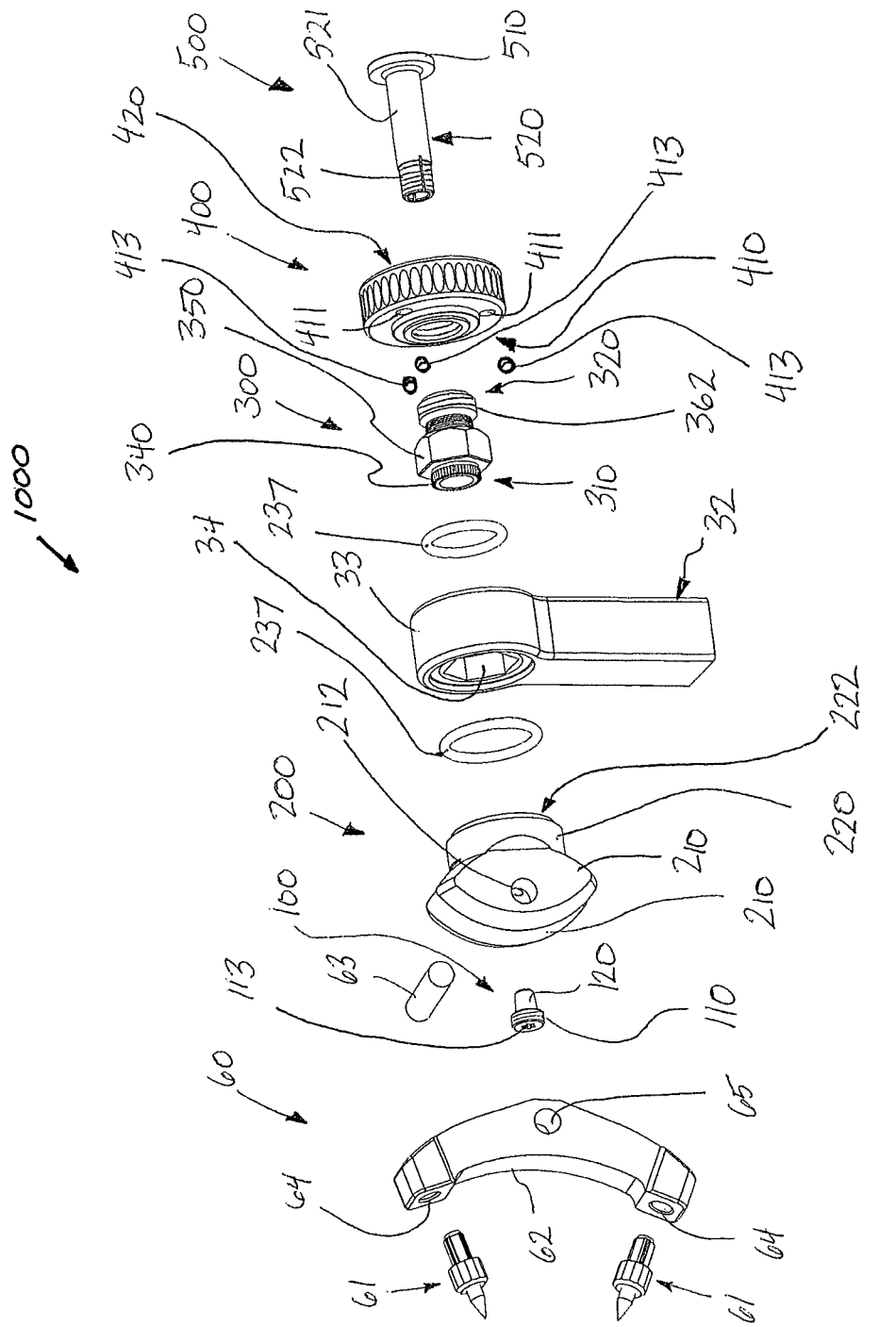
FIG. 3 depicts an exploded view of the locking apparatus of FIG. 2.
Figure 4:
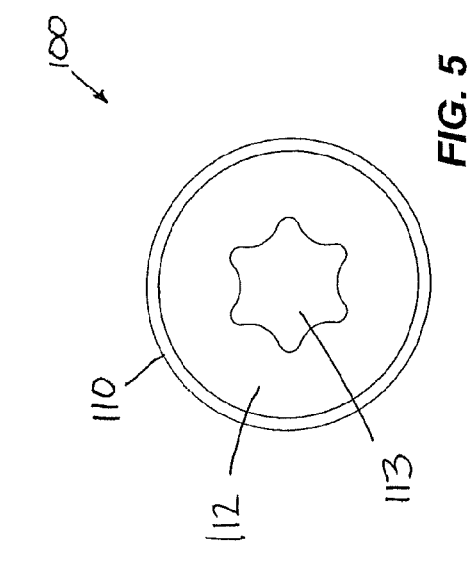
FIG. 4 depicts a perspective view of the exemplary center insert of FIG. 3.
Figure 5:
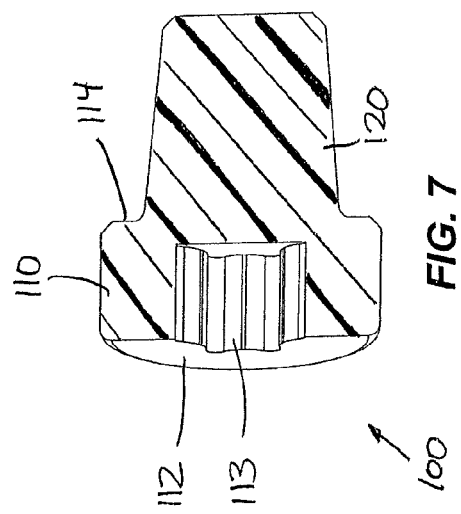
FIG. 5 depicts an end view of the center insert of FIG. 3.
Figure 6:
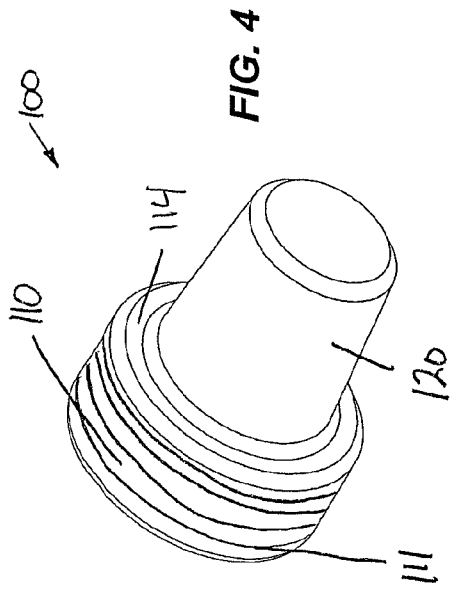
FIG. 6 depicts a side view of the center insert of FIG. 3.
Figure 7:
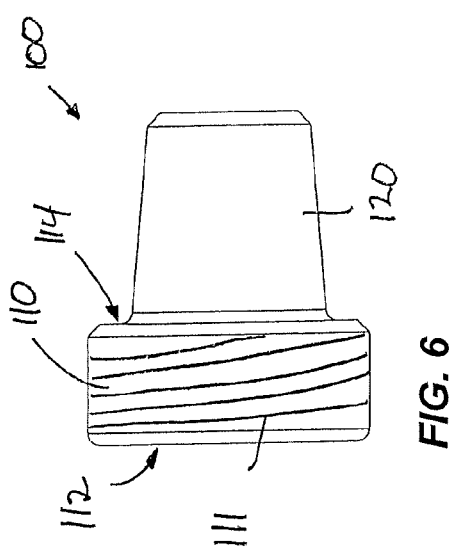
FIG. 7 depicts a perspective view, shown in cross section, of the center insert of FIG. 3.
Figure 8:
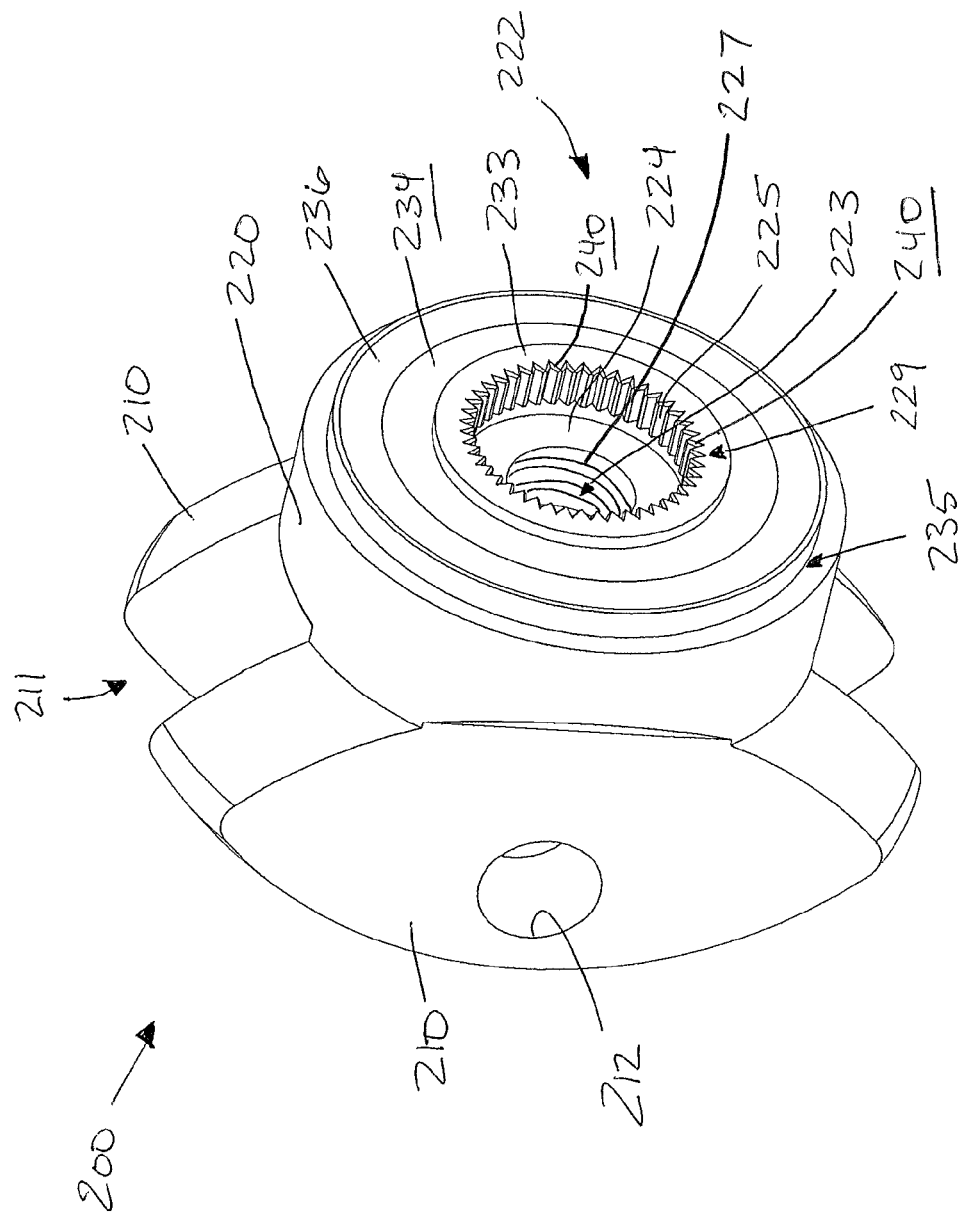
FIG. 8 depicts a perspective view of the exemplary arch member of FIG. 3.
Figure 10:
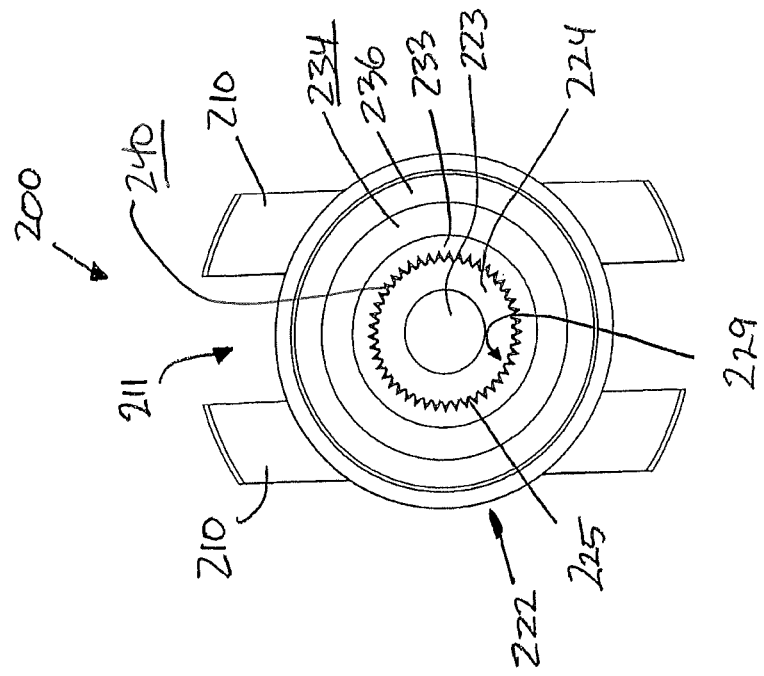
FIG. 10 depicts another end view of the arch member of FIG. 3, showing the opposite end to that shown in FIG. 9.
Figure 9:
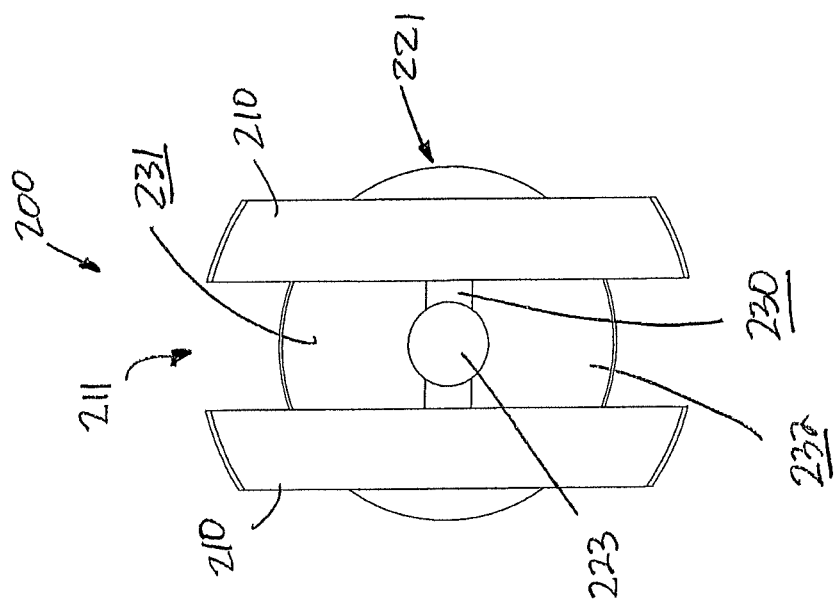
FIG. 9 depicts an end view of the arch member of FIG. 3.
Figure 12:
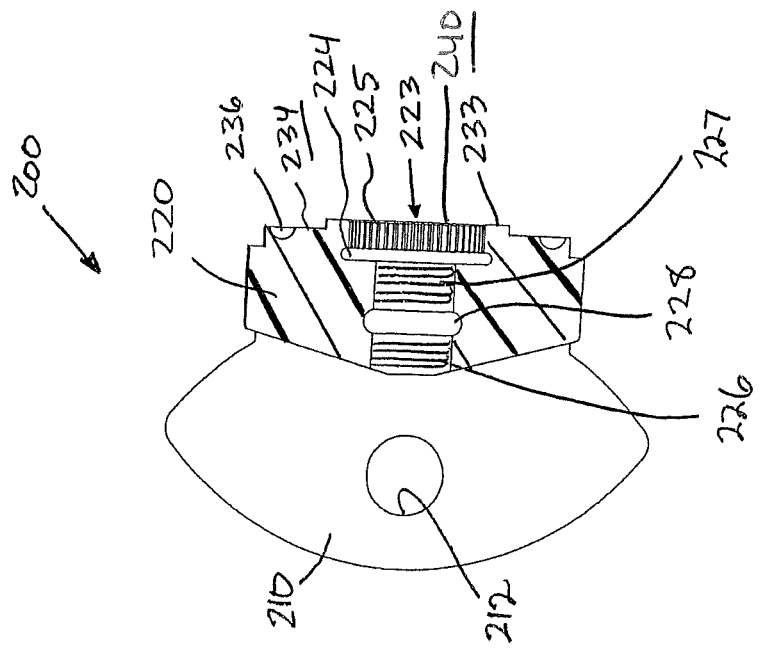
FIG. 12 depicts a side view, shown in cross section, of the arch member of FIG. 3.
Figure 11:
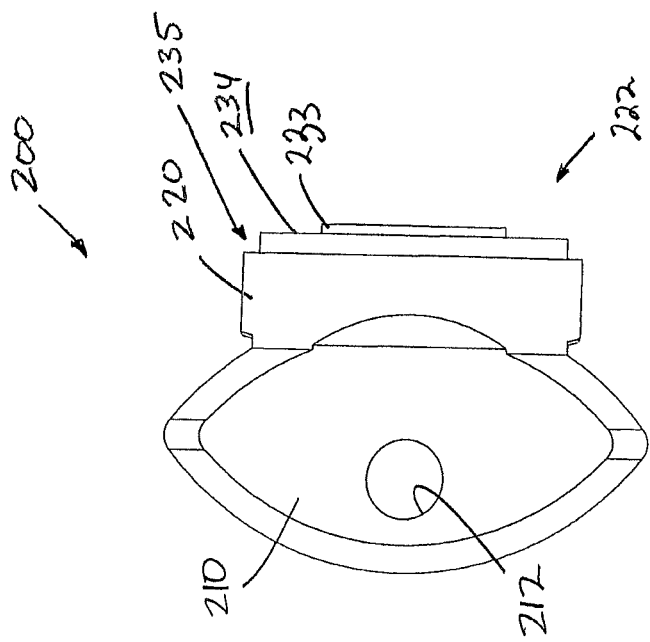
FIG. 11 depicts a side view of the arch member of FIG. 3.

FIGS. 2 and 3 illustrate an exemplary locking apparatus (1000) of skull clamp (10). Locking apparatus (1000) is configured such that dual pin fixture (60) is connected to arm (30) at end (33) in a secure, yet adjustable manner. As shown in the present example, locking apparatus (1000) comprises dual pin fixture (60), center insert (100), arch member (200), second arm (30) of skull clamp (10), connector (300), disc (400), and bolt (500). These components will be described in greater detail in the following paragraphs.

A. Exemplary Dual Pin Fixture

Still referring to FIGS. 2 and 3, dual pin fixture (60) comprises skull pins (61), rocker arm (62), and connecting pin (63). As shown, skull pins (61) fit within recesses (64) of rocker arm (62). Connecting pin (63) is positionable within opening (65) of rocker arm (62), and connecting pin (63) permits selective rotation of rocker arm (62) about connecting pin (63). In view of the teachings herein, other structures, configurations, and features of dual pin fixture (60) will be apparent to those of ordinary skill in the art. By way of example only, rocker arm (62) can be configured in different sizes and/or with different angles to provide for a suitable fit with a patient.

B. Exemplary Center Insert

FIGS. 4-7 illustrate center insert (100) of locking apparatus (1000). Center insert (100) comprises a collar (110) and a tapered portion (120). In the present example, collar (110) includes external threads (111) located about the circumference of collar (110). Collar (110) further includes an end (112) having a recess (113). Recess (113) is configured as a driving feature that permits center insert (100) to be rotated. In the present example, recess (113) is a hexalobular internal driving feature, also known as a star driving feature; of course other configurations for recess (113) will be apparent to those of ordinary skill in the art in view of the teachings herein. Collar (110) includes flange (114) that connects with tapered portion (120). As shown, flange (114) is configured with a greater diameter than the widest part of tapered portion (120). In the present example, tapered portion (120) is a solid, substantially rigid, piece that is configured to insert within bolt (500) as will be described further below.

C. Exemplary Arch Member

FIGS. 8-12 illustrate arch member (200) of locking apparatus (1000). Arch member (200) comprises arches (210) and a body (220). Arches (210) connect to body (220) and extend outwardly from the connection area with body (220). Arches (210) are spaced apart from one another such that a gap (211) is defined between arches (210). Arches (210) each comprise an opening (212), with the openings (212) being generally aligned, and configured to receive connecting pin (63) of dual pin fixture (60) to thereby attach rocker arm (62) and associated pins (61) to arch member (200).

Body (220) of arch member (200) comprises a first end (221), a second end (222), a passage (223) extending between first and second ends (221, 222), a recessed interior flange (224), and a recessed toothed portion (225) or starburst feature. Passage (223) includes a first interior threaded portion (226), a second interior threaded portion (227), and a divider (228) positioned between first and second interior threaded portions (226, 227). In the present example, divider (228) is configured as a non-threaded portion within passage (223) with a larger diameter than the surrounding first and second interior threaded portions (226, 227). As will be discussed in greater detail below, first interior threaded portion (226) is configured to engage with external threads (111) of center insert (100).

Moving through passage (223) from first end (221) of body (220) to second end (222) of body (220), passage (223) connects with, and passes through, recessed interior flange (224). Still moving through passage (223) toward second end (222), passage (223) further connects with, and passes through, recessed toothed portion (225). Recessed toothed portion (225), sometimes referred to herein as a starburst feature, comprises a plurality of teeth (229) that project inward axially toward an axis defined by passage (223). Teeth (229) each comprise chamfer surface (240) nearest second end (222) of body (220). Chamfer surface (240) defines an angled surface on each side of a tooth that connects the surface of lip (233) with the surface of recessed toothed portion (225). In some versions, chamfer surface (240) assists in guiding a portion of connector (300) into engagement with recessed toothed portion (225) as will be discussed further below. In some versions, chamfer surface (240) provides additional surface area for securing connector (300) as will be discussed further below.

In the present example, first end (221) is configured with a first surface (230) that is generally parallel with a first surface (234) of second end (222). First end (221) further is configured with second and third surfaces (231, 232) that extend from first surface (230) and are generally non-parallel with the first surface (234) of second end (222). As best seen in the cross section view of FIG. 12, with the above configuration second and third surfaces (231, 232) of first end (221) have a sideways "V" profile with the intersecting point of the "V" positioned most closely toward arches (210). In the present example, second end (222) is configured with a lip (233), first surface (234), and notches (235). Lip (233) surrounds and projects outward from passage (223) where recessed toothed potion (225) begins. First surface (234) of second end (222) comprises a circular groove (236) for receiving an o-ring (237) as seen in the exploded view of FIG. 3. When locking apparatus (1000) is assembled, o-ring (237) has a compressive fit against end (33) of second arm (30) of skull clamp (10). Notches (235) are configured such that when locking apparatus (1000) is assembled, a close fit with second arm (30) is attained as will be discussed further below.

D. Exemplary End of Skull Clamp Arm

Figure 14:
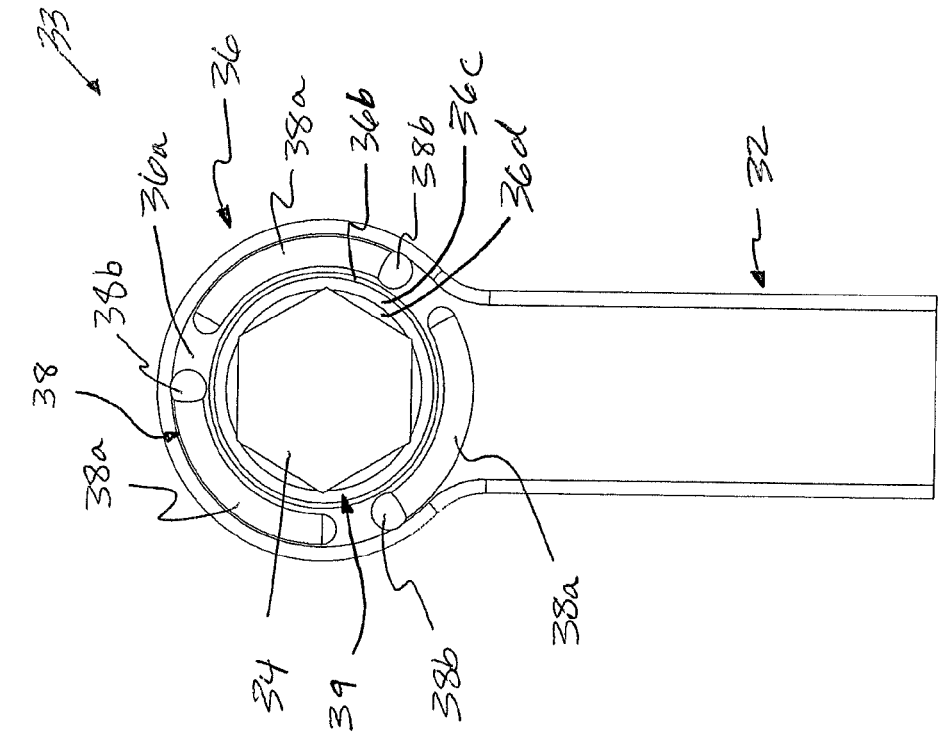
FIG. 14 depicts another end view of the upper portion of the skull clamp arm of FIG. 3, showing the opposite end to that shown in FIG. 13.
Figure 13:
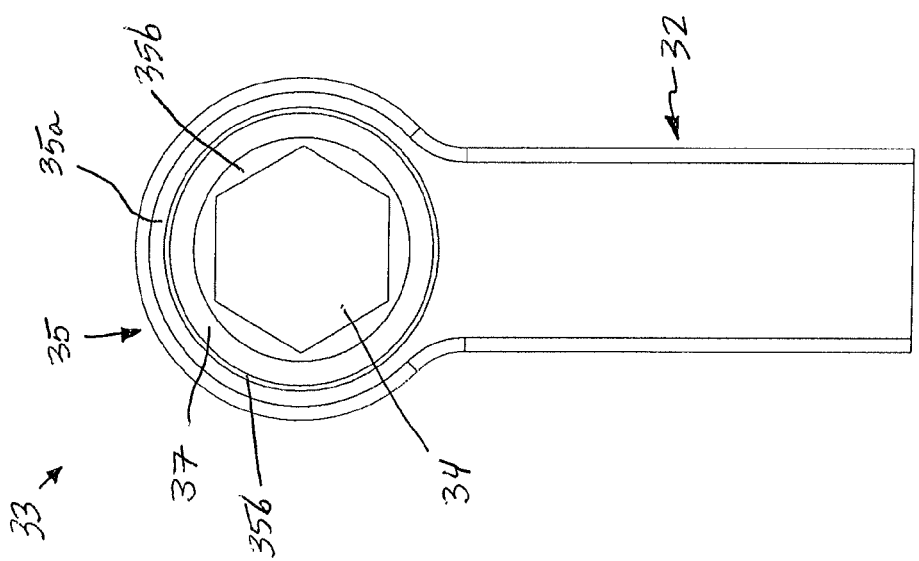
FIG. 13 depicts an end view of the upper portion of the exemplary skull clamp arm of FIG. 3.
Figure 15:
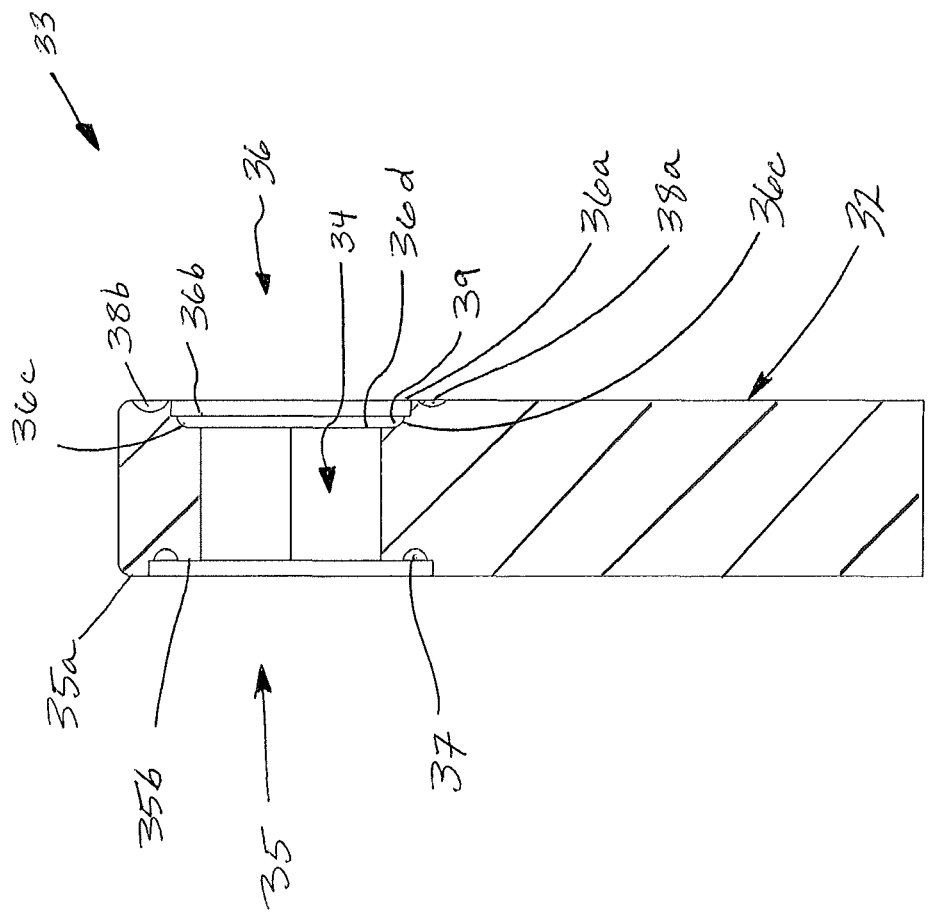
FIG. 15 depicts a front view, shown in cross section, of the upper portion of the skull clamp arm of FIG. 3.
Figure 17:
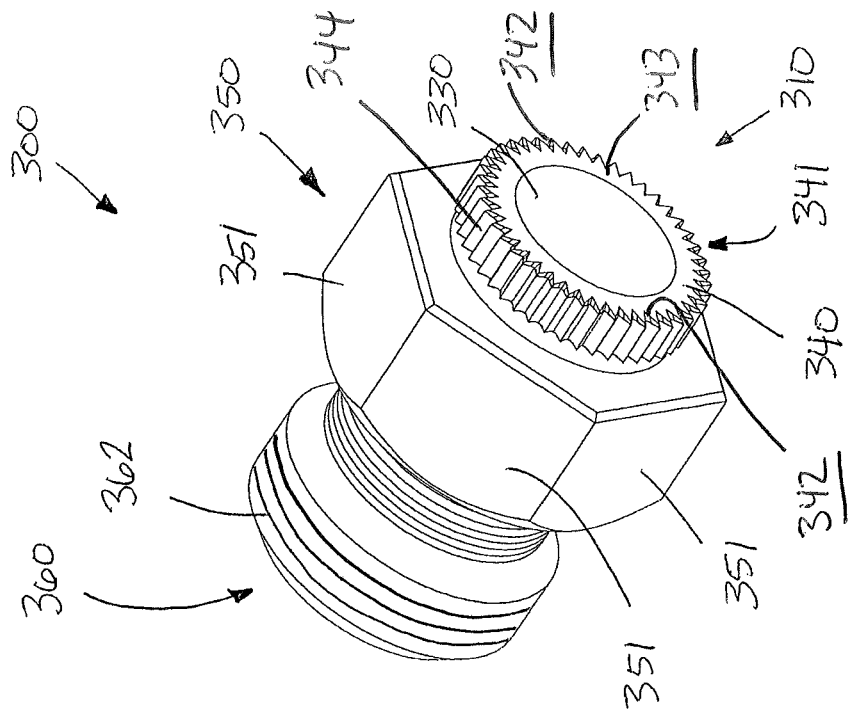
FIG. 17 depicts another perspective view of the connector of FIG. 3.
Figure 16:
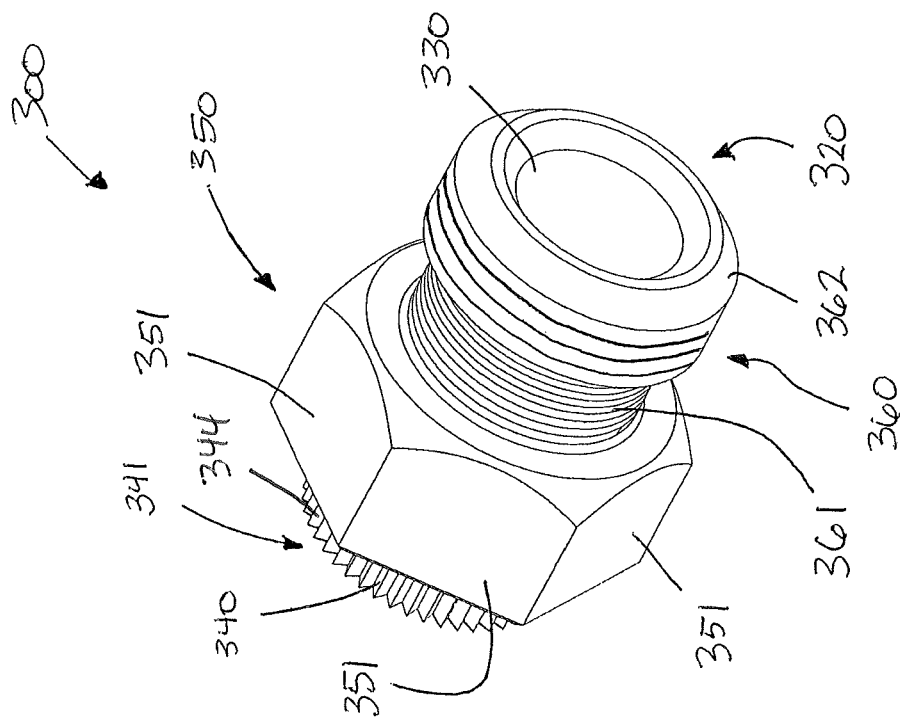
FIG. 16 depicts a perspective view of the exemplary connector of FIG. 3.
Figure 19:
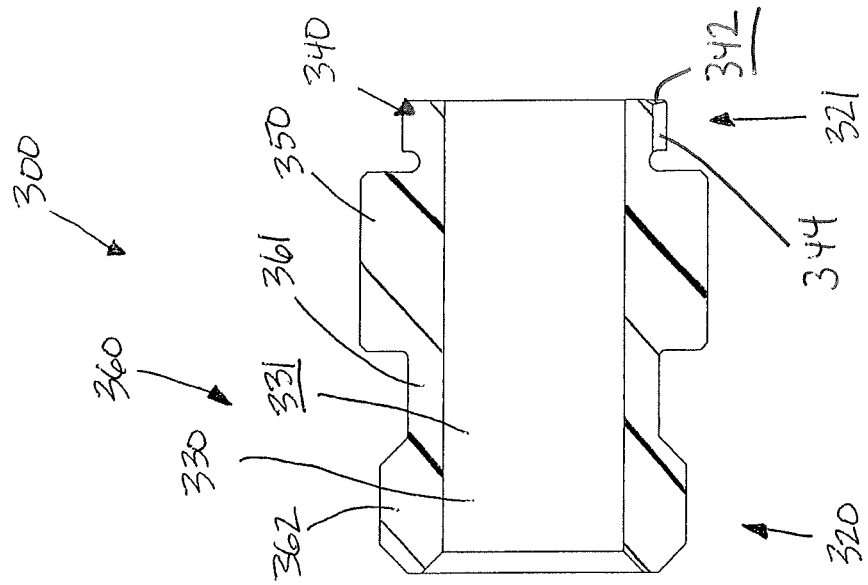
FIG. 19 depicts a side view, shown in cross section, of the connector of FIG. 3.
Figure 18:
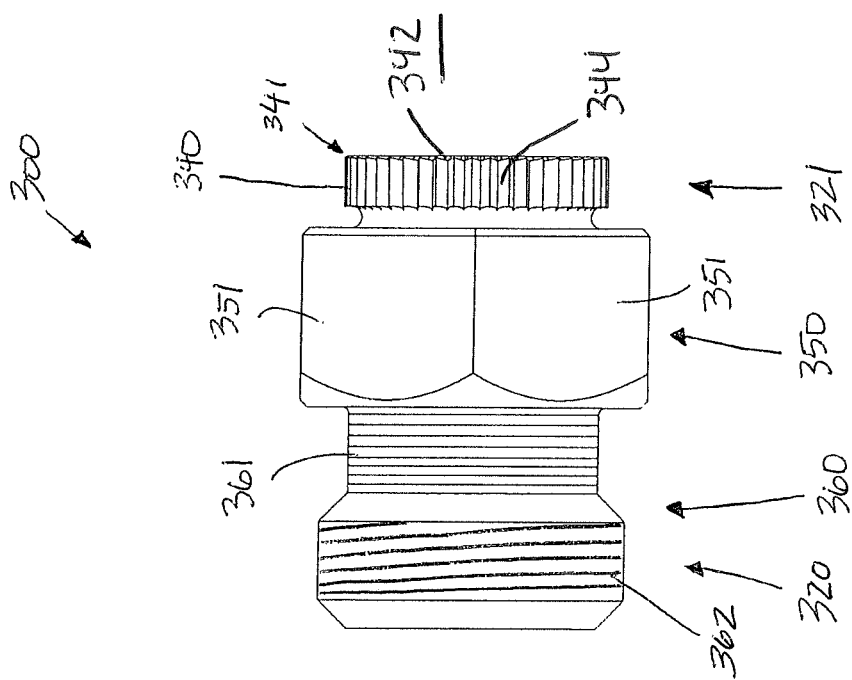
FIG. 18 depicts side view of the connector of FIG. 3.

FIGS. 13-15 illustrate end (33) of second arm (30) of skull clamp (10). End (33) comprises an opening (34), a first end portion (35), and a second end portion (36). In the present example, opening (34) extends through end (33) from first end portion (35) to second end portion (36), and opening (34) is configured with a hexagon shaped internal opening. In some other versions, opening (34) can have other shapes, e.g., triangular, square, pentagonal, star-shaped or hexalobular, non-circular, and other shapes that will be apparent to one of ordinary skill in the art in view of the teachings herein. First end portion (35) comprises a first surface (35a) and a second surface (35b). In the present example, first surface (35a) is an outermost surface defining the outer edge of first end portion (35). Second surface (35b) is recessed relative to first surface (35a). Second surface (35b) comprises a circular groove (37) configured to receive o-ring (237) that is positioned between second arm (30) and arch member (200) when locking apparatus (1000) is assembled. In the present example groove (37)

is continuous and is located about opening (34). In the present example, on first end portion (35), opening (34) is positioned within second surface (35b).

Second end portion (36) comprises a first surface (36a), a second surface (36b), a curved transition (36c), and a third surface (36d). In the present example, first surface (36a) is an outermost surface defining the outer edge of second end portion (36). First surface (36a) comprises a circular groove (38) that is positioned between second arm (30) and disc (400) when locking apparatus (1000) is assembled. In the present example groove (38) is located around opening (34) and is divided into sections (38a) with each section (38a) including a generally circular recess (38b). Circular recesses (38b) are configured to receive a sphere (413) positionable within circular recesses (411) of disc (400) as described further below and as seen in FIG. 3. This engagement between spheres (413) of disc (400) and circular recesses (38b) of second end portion (36) serve as a stop when turning disc (400) from an open position to a lock position and vice-versa as described further below. Second surface (36b) is recessed relative to first surface (36a). Third surface (36d) is recessed relative to second surface (36b), and between second surface (36b) and third surface (36d) is a curved transition (36c). Curved transition (36c) defines a space (39) configured to receive o-ring (237) that is positioned between second arm (30) and disc (400) when locking apparatus (1000) is assembled. In the present example, on second end portion (36), opening (34) is positioned within third surface (36d) and slightly extends into curved transition (36c) at the outer peaks of the hexagon shaped opening. In some other versions, opening (34) is entirely positioned within thrid surface (36d) without extending into curved transition (36c).

E. Exemplary Connector

FIGS. 16-19 illustrate connector (300) of locking apparatus (1000). Connector (300) comprises first end (310), second end (320), passage (330), first engaging member (340), second engaging member (350), and coupling (360). Passage (330) extends from first end (310) through connector (300) to second end (320). In the present example passage (330) has a smooth interior wall (331).

At first end (310) is first engaging member (340). In the present example, first engaging member (340) comprises toothed portion (344) or starburst feature that comprises a plurality of teeth (341) that project outward axially from an axis defined by passage (330). Teeth (341) each comprise chamfer surface (342) nearest the portion of first engaging member (340) closest to first end (310). Chamfer surface (342) defines an angled surface on each side of a tooth that connects an end surface (343) of first engaging member (340) with the surface of toothed portion (344). In some versions, chamfer surface (342) assists in guiding connector (300) into engagement with recessed toothed portion (225) of arch member (200) as will be discussed further below. In some versions, chamfer surface (342) provides additional surface area for securing connector (300) as will be discussed further below.

Second engaging member (350) is positioned between first engaging member (340) and second end (320) of connector (300). Second engaging member (350) is configured as a hexagonally shaped externally projecting body. In its hexagonal shape, second engaging member (350) comprises faces (351) along its perimeter. As will be described in greater detail below, first engaging member (340) is configured to engage recessed toothed portion (225) of arch member (200), and second engaging member (350) is configured to engage opening (34) of arm (30) of skull clamp (10).

At second end (320) is coupling (360). Coupling (360) comprises a neck (361) and collar (362). In the present example, the dimensions and proportions of coupling (360), passage (330), first engaging member (340), and second engaging member (350) are configured such that connector (300) is insertable within opening (34) of second arm (30). In some versions, as will be discussed in greater detail below, the insertion of connector (300) within opening (34) is such that connector (300) cannot pass through opening (34); of course in some other versions connector (300) may be modified such that connector (300) could pass through opening (34). Also, in the present example, collar (362) is threaded such that connector (300) threadably engages a corresponding threaded portion (431) of disc (400) as discussed further below.

F. Exemplary Disc

Figures 20, 21:
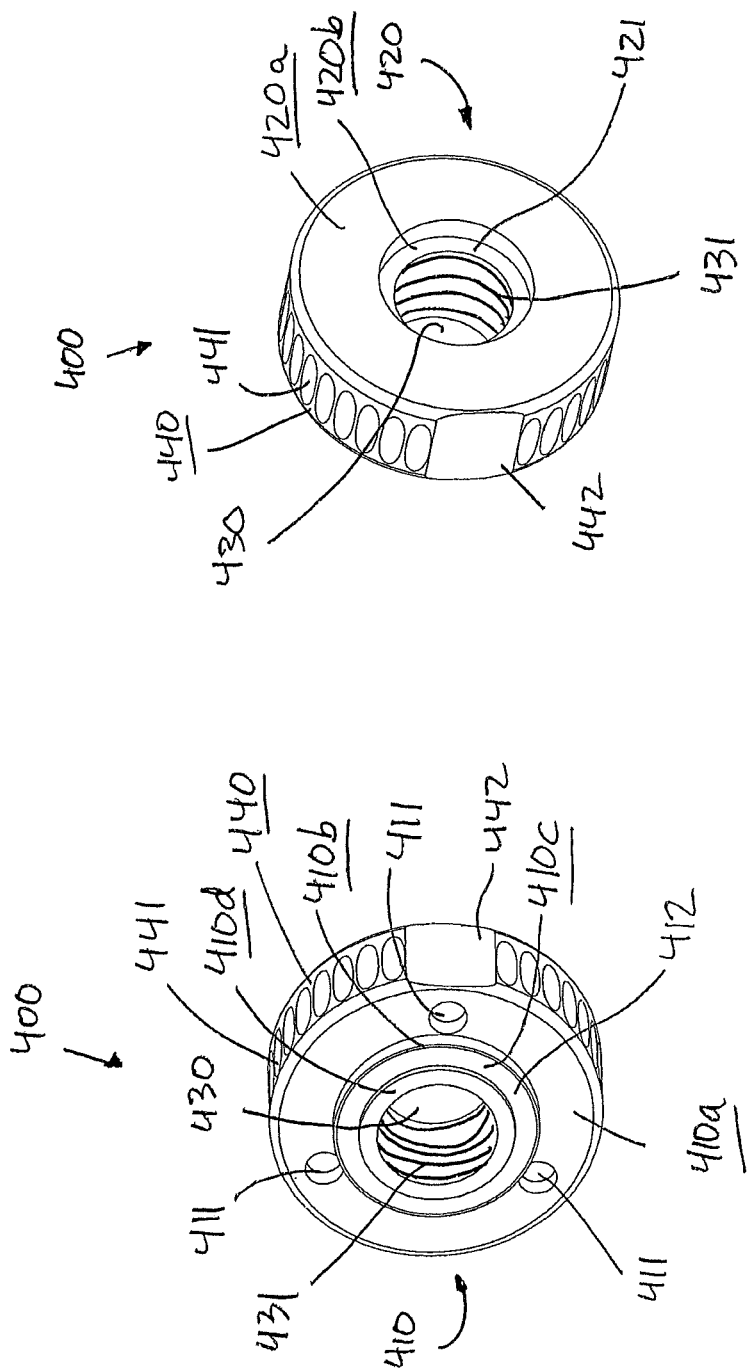
FIG. 20 depicts a perspective view of the exemplary disc of FIG. 3.
FIG. 21 depicts another perspective view of the disc of FIG. 3.
Figure 24:
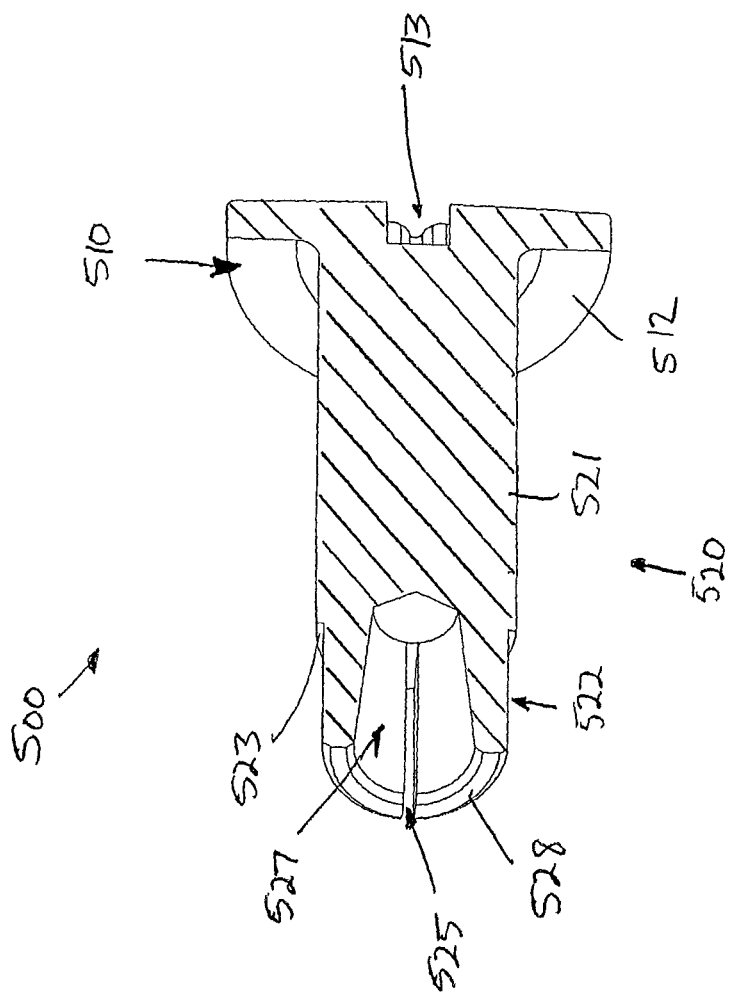
FIG. 24 depicts a perspective view, shown in cross section, of the bolt of FIG. 3.
Figure 25:
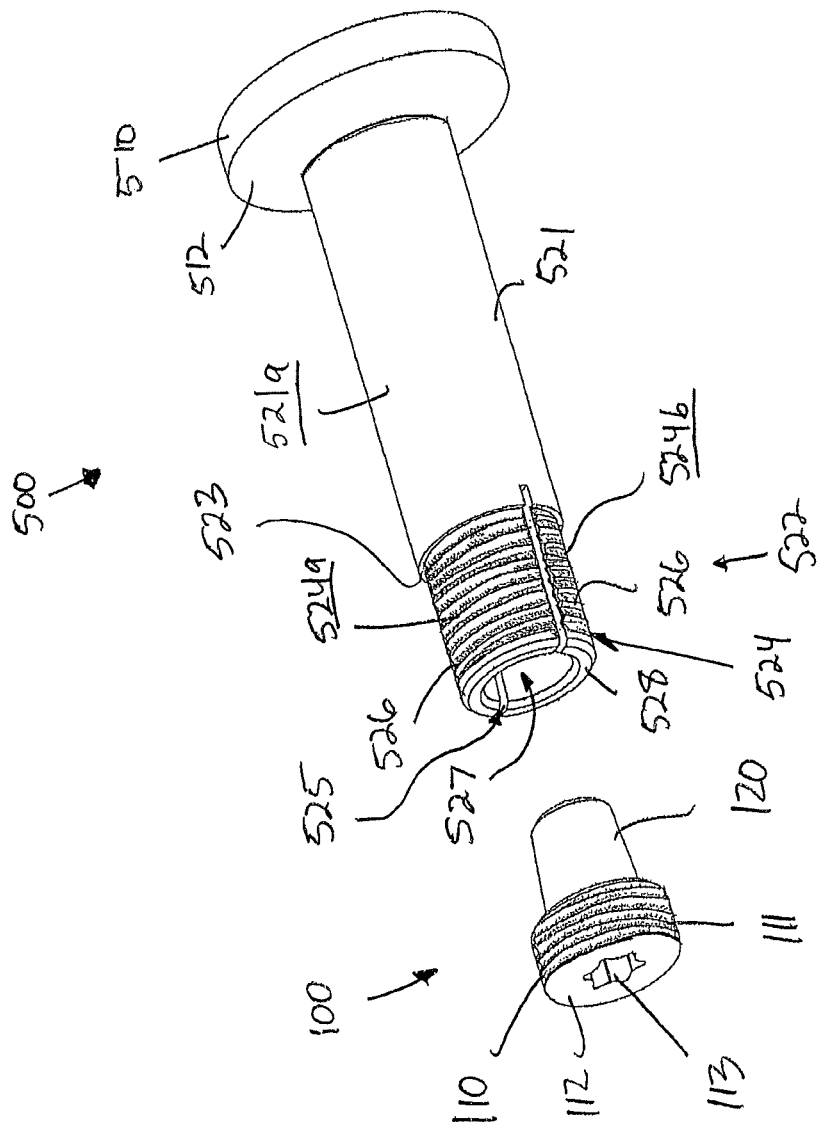
FIG. 25 depicts a perspective view of the exemplary bolt of FIG. 3, shown with the center insert of FIG. 3.

FIGS. 20 and 21 illustrate disc (400) of locking apparatus (1000). Disc (400) comprises first end (410), second end (420), and passage (430). Passage (430) extends from first end (410) through disc (400) to second end (420). In the present example passage (430) has a threaded interior (431) that is configured to engage with the threads of collar (362) of connector (300). With this threaded engagement, as will be discussed in greater detail below, rotating disc (400) causes connector (300) to translate along an axis defined by passage (430), and further causes rocker arm (62) to lock or unlock depending on the direction of rotation.

First end (410) of disc (400) comprises first surface (410a), second surface (410b), curved transition (410c), and third surface (410d). First end (410) further comprises circular recesses (411) located within first surface (410a). Circular recesses (411) house spheres (413) as shown in FIG. 3. As mentioned previously, spheres (413) are configured to engage with groove (38) of end (33) of second arm (30) to control rotation of disc (400) relative to second arm (30). Spheres (413) slide along groove (38) when rotating disc (400) until reaching a stop point at corresponding circular recesses (38b) of groove (38). In the present example, first surface (410a) is positioned about passage (430), and is spaced from passage (430) by other surfaces (410b, 410c, and 410d). Second surface (410b) protrudes outward from first surface (410a), and thrid surface (410d) protrudes outward from second surface (410b). Between second surface (410b) and third surface (410d) is curved transition (410c). Curved transition (410c) defines a recessed groove (412) configured to receive o-ring (237) that is positioned between second arm (30) and disc (400) when locking apparatus (1000) is assembled. As will be discussed further below, the protruding configuration of second and third surfaces (410b, 410d) are such that these surfaces (410b, 410d) of disc (400) fit closely with the recessed surfaces (36b, 36d) of second end portion (36) of second arm (30).

Second end (420) of disc (400) comprises first surface (420a) and second surface (420b). In the present example, first surface (420a) is positioned about passage (430), and is spaced from passage (430) by second surface (420b). Second surface (420b) is recessed relative to first surface (420a) and defines a shelf (421). As described further below, shelf (421) provides space for head (510) of bolt (500) such that outer surface (511) of bolt (500) is planar with first surface (420a) of disc (400) when locking apparatus (1000) is assembled.

Disc (400) further comprises a lateral surface (440) defining a perimeter of disc (400). Lateral surface (440) comprises grips (441) spaced about the perimeter that, in the present example, have an oval shape. Lateral surface (440) also comprises flat edge (442) that can serve as a reference point along lateral surface (440). Flat edge (442) can also include markings (e.g., arrows) to indicate the direction to rotate disc (400) to lock or unlock locking apparatus (1000).

G. Exemplary Bolt

FIGS. 22-25 illustrate bolt (500) of locking apparatus (1000). Bolt (500) comprises head (510) and shaft (520). Head (510) comprises outer surface (511) and inner surface (512). Outer surface (511) of head (510) includes a recess (513). Recess (513) is configured as a driving feature that permits bolt (500) to be rotated. In the present example, recess (513) is a hexalobular internal driving feature, also known as a star driving feature; of course other configurations for recess (513) will be apparent to those of ordinary skill in the art in view of the teachings herein.

Shaft (520) comprises a first section (521) and a second section (522). First section (521) connects to head (510). First section (521) has an outer surface (521a) that, in the present example, is smooth. Formed at an end (523) of first section (521) is second section (522). Second section (522) has a split outer surface (524) that includes first half (524a) and second half (524b). Split outer surface (524) is defined by a slot (525) that passes longitudinally though second section (522) of shaft (520). In the present example, slot (525) further extends partially through first section (521) of shaft (520). In the present example, first half (524a) and second half (524b) of split outer surface (524) include threads (526). As will be described in greater detail below, threads (526) are configured to engage with second interior threaded portion (227) of arch member (200).

Shaft (520) further comprises a void space (527) that begins at an end (528) of second section (522) and extends within shaft (520). In the present example, void space (527) extends through all of second section (522) and into a portion of first section (521). Also, void space (527) has a tapered profile, with the largest diameter of void space (527) being located at end (528). As will be discussed in greater detail below, void space (527) is configured such that when locking apparatus (1000) is assembled, tapered portion (120) of center insert (100) fits closely within void space (527). As shown in the present examples, tapered portion (120) of center insert (100) and void space (527) have corresponding shapes such that a close fit is achieved. In view of the teachings herein, other configurations, besides a tapered configuration, for the interface between center insert (100) and shaft (520) can be used and will be apparent to those of ordinary skill in the art.

H. Exemplary Use of Locking Apparatus

Figure 26:
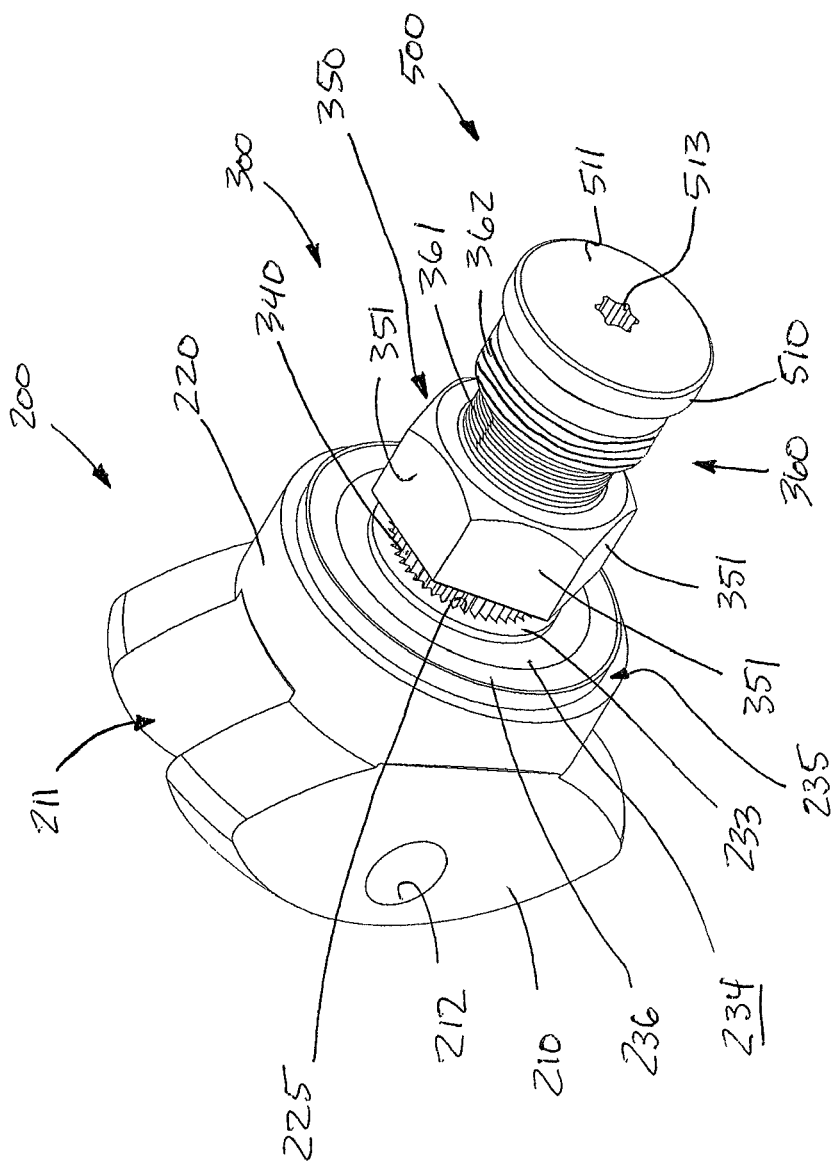
FIG. 26 depicts a perspective view of the locking apparatus of FIG. 3, shown without the dual pin fixture, skull clamp arm, and disc.
Figure 27:
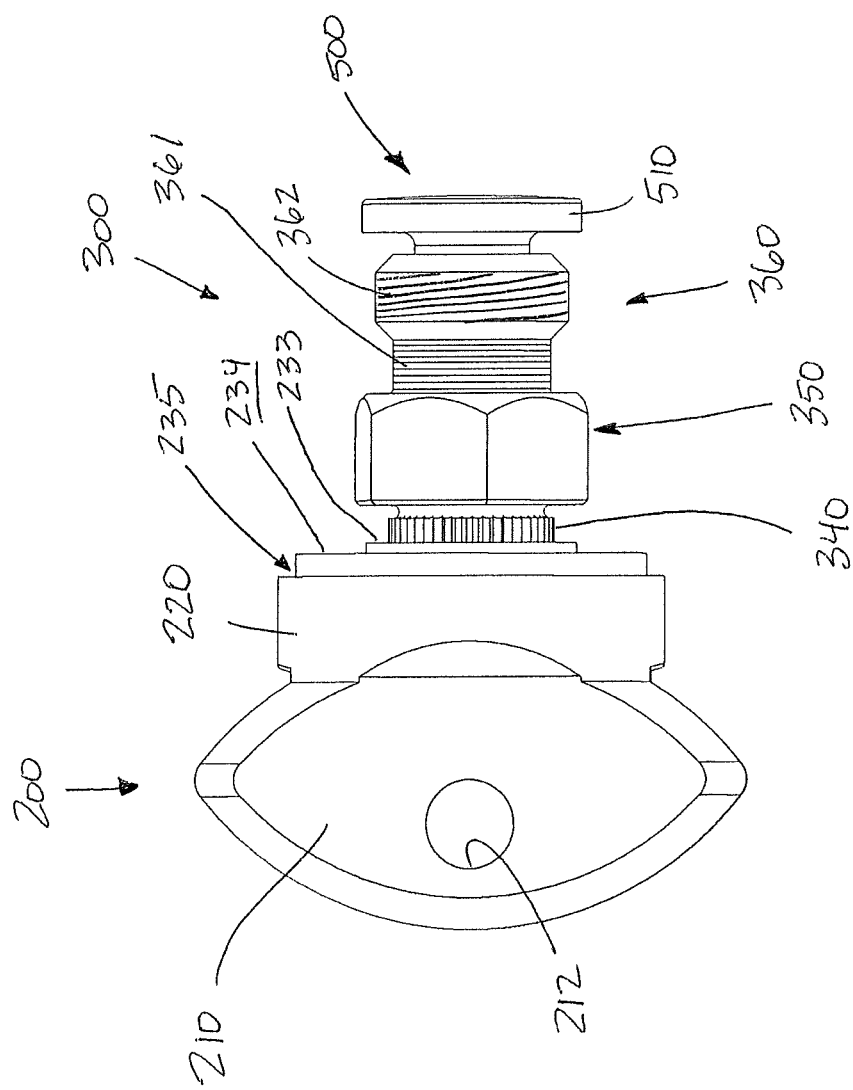
FIG. 27 depicts a side view of the components of the locking apparatus as shown in FIG. 26.
Figure 28:
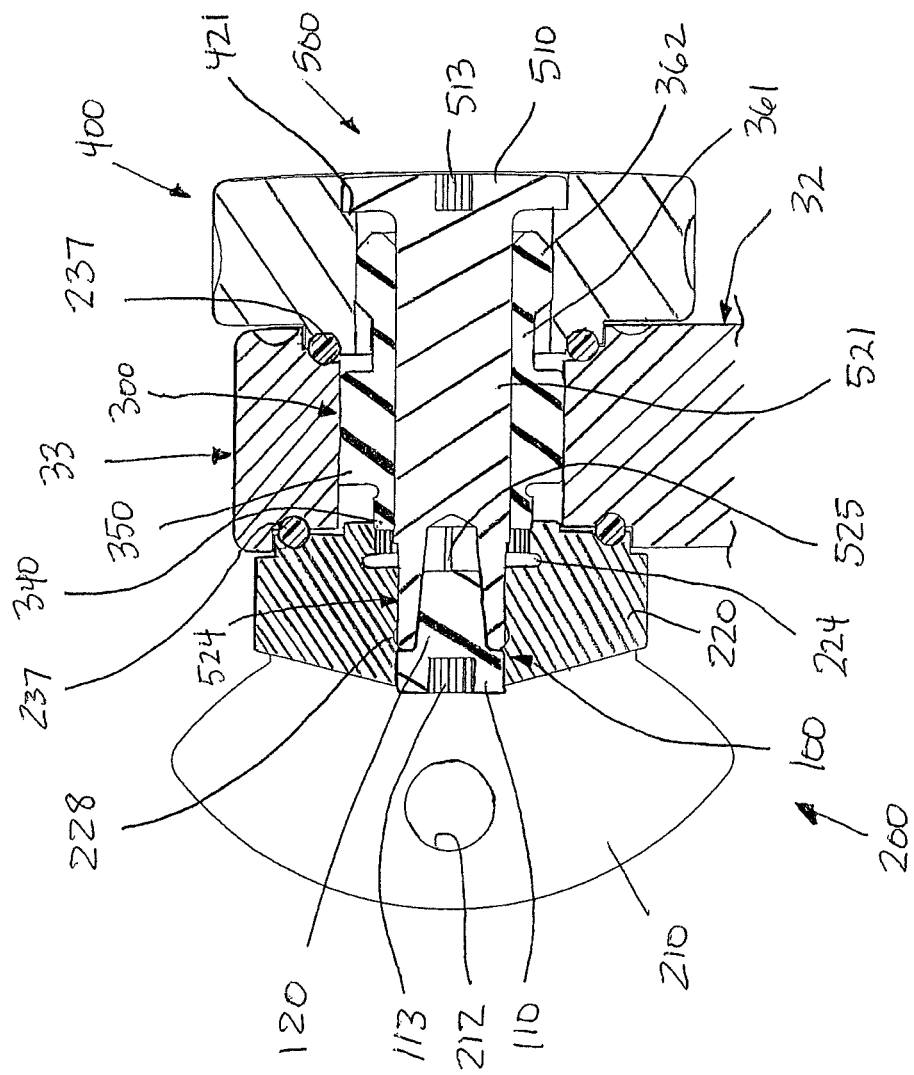
FIG. 28 depicts a side view, shown in cross section, of the locking apparatus of FIG. 26, shown with the skull clamp arm, and disc attached.

FIGS. 26-28 illustrate select assembled components of locking apparatus (1000) to better illustrate locking apparatus (1000) in an exemplary use. As mentioned previously, external threads (111) on collar (110) of center insert (100) are threadably engaged with first interior threaded portion (226) of arch member (200). In the present example this engagement is accomplished using recess (113) and its internal driving feature. In the initial assembly of locking apparatus (1000), center insert (100) is not tighten or threadably installed to its final assembled position. As discussed further below, final tightening of center insert (100) within arch member (200) is completed after bolt (500) tightening with respect to arch member (200) has been set. In some versions, center insert (100) is not installed at all until bolt (500) tightening with respect to arch member (200) has been set.

With center insert (100) within arch member (200), arch member (200) is positioned adjacent first end portion (35) of second arm (30) of skull clamp (10). In this arrangement, passage (223) of arch member (200) aligns with opening (34) of second arm (30). O-ring (237) is positioned within groove (37) of first end portion (35) and is thus positioned between arch member (200) and second arm (30).

With arch member (200) and second arm (30) in the above orientation, passage (330) of connector (300) is aligned with passage (223) of arch member (200) and opening (34) of second end portion (36) of second arm (30). Connector (300) is inserted within opening (34) from second end portion (36) such that first engaging member (340) passes through opening (34), and second engaging member (350) fits within opening (34). As mentioned previously, second engaging member (350) has a corresponding shape to the shape of opening (34). The corresponding shapes of second engaging member (350) and opening (34) are such that connector (300) cannot rotate relative to second arm (30) when second engaging member (350) is within opening (34). However, the corresponding shapes of second engaging member (350) and opening (34) are such that second engaging member (350) (and hence connector (300)) can translate longitudinally along a longitudinal axis defined by opening (34). In the present example, the corresponding shapes are hexagonal; of course other shapes, (e.g., triangular, square, pentagonal, star-shaped or hexalobular, non-circular, among others) may be used. In this arrangement, teeth (341) of first engaging member (340) of connector (300) are proximate with corresponding teeth (229) of recessed toothed portion (225) of arch member (200).

In some versions, connector (300) and second arm (30) are configured such that connector (300) is insertable within second arm (30) from only one end; of course in other versions connector (300) may be configured to be insertable with second arm (30) from either end. Such one-side insertability may provide ease and intuitive assembly. In one version, the sizes and proportions of coupling (360), first engaging member (340), and opening (34) are such that connector (300) is insertable from only second end portion (36) of second arm (30). For instance, first engaging member (340) is small enough to fit through opening (34), but coupling (360) is too large to fit through opening (34). Such an arrangement as described here further provides that once connector (300) is inserted within second arm (30), connector (300) cannot completely pass through opening (34), as collar (362) of coupling (360) would contact thrid surface (36d) of second end portion (36) thereby acting as a stop.

Disc (400) is threaded onto collar (362) of connector (300) with interior threaded portion (431) of passage (430) receiving the threads of collar (362). Bolt (500) is configured for insertion through passage (430) of disc (400) and through passage (330) of connector (300). In the present example, when fully inserted, head (510) of bolt (500) is configured to contact shelf (421) of disc (400) thereby preventing bolt (500) from completely passing through passage (430). In this arrangement, the shaft (520) of bolt (500) extends into passage (223) of arch member (200). With shaft (520) through connector (300) and within arch member (200), disc (400) is positioned adjacent second end portion (36) of second arm (30), with o-ring (237) positioned within space (39) of second end portion (36) and thus between disc (400) and second arm (30). Spheres (413) of disc (400) are positioned within groove (38) as mentioned above, and spheres (413) are operably configured to slide along groove (38) within respective sections (38a) of groove (38) when disc (400) is rotated as described more below.

As illustrated best in FIG. 28, with the above described arrangement, threads (526) of second section (522) of bolt (500) are threadably engaged with second interior threaded portion (227) of arch member (200). This threaded engagement is accomplished using the internal driving feature of recess (513) of bolt (500). This threaded arrangement between second section (522) of bolt (500) and second interior threaded portion (227) of arch member (200) permits locking apparatus (1000) to be tightened by drawing arch member (200) and disc (400) towards each other while compressing against o-rings (237) of second arm (30). In the present example, tightening bolt (500) too much can result in greater force required to rotate disc (400) to lock and unlock arch member (200) for rotation purposes and adjustment of rocker arm (62). Not tightening bolt (500) enough can result in a loose assembly where arch member (200) could rotate inadvertently. Thus once a suitable degree of tightening of bolt (500) is achieved, center insert (100) is tightened further to its final assembled position such that center insert (100) fits within void space (527) of bolt (500) to maintain the desired degree of tightening as discussed further below.

As bolt (500) is tightened, the configuration of shaft (520) having split outer surface (524) in combination with the tapered profile of void space (527) and tapered portion (120) of center insert (100), create lateral forces that are directed generally perpendicular to the longitudinal axis defined by bolt (500), and in substantially all directions (e.g., substantially all directions perpendicularly outward from the longitudinal axis—thus a substantially uniform force distribution outward from the axis). In other words, when being tightened, as center insert (100) moves further toward bolt (500), tapered portion (120) pushes laterally outward on split outer surface (524) of bolt (500) from a center axis defined by bolt (500) and common to tapered portion (120). These lateral forces created from this motion cause second section (522) and a portion of first section (521) of shaft (520) of bolt (500) to flex outward thereby securing the setting for the tightness of bolt (500). In the present example, this outward flexing motion of shaft (520) creates a compression fit between second section (522) and passage (223) of arch member (200) (e.g., the compression fit is in addition to the threaded fit between second section (522) and second interior threaded portion (227) of arch member (200)). With this combined threaded and compression fit between arch member (200) and bolt (500), arch member (200) and bolt (500) rotate in unison when locking apparatus (1000) is in the unlocked state and arch member (200) rotated to a desired position. Such synchronized rotation permits a desired position for arch member (200) to be achieved without the rotation of arch member (200) causing either over-tightening with bolt (500) or unintended loosening with bolt (500).

When bolt (500) is fully inserted and tightened, inner surface (512) of bolt (500) contacts shelf (421) of disc (400). This contact in conjunction with the threaded configuration of second section (522) and second interior threaded portion (227) as described above hold disc (400) in position relative to arch member (200). In this assembled state, disc (400) is rotatable such that rotation of disc (400) causes connector (300) to translate longitudinally along an axis common to and defined by passages (223, 330, 430) due to connector's (300) threaded engagement with disc (400). The translation of connector (300) moves connector (300) from a position locking arch member (200), to a position unlocking arch member (200) such that arch member (200) can be rotated. For instance, when disc (400) is rotated such that connector (300) is translated toward arch member (200), teeth (341) of connector (300) engage teeth (229) of arch member (200), thereby securing the rotational position of arch member (200). When disc (400) is rotated in the opposite direction such that connector (300) is translated away from arch member (200), teeth (341) of connector (300) disengage teeth (229) of arch member (200), thereby permitting the rotational position of arch member (200) to be adjusted. In some versions, chamfer surface (342) on teeth (341) of connector (300) and chamfer surface (240) on teeth (229) of arch member (200) enhance the adjustment of arch member (200) by guiding teeth (341) and teeth (229) into engagement. In the present example arch member (200) is rotatable 360 degrees.

As dual pin fixture (60) is connected with arch member (200), dual pin fixture (60) is rotatably adjustable by these operations. Furthermore, as mentioned above dual pin fixture (60) is pivotable about connecting pin (63) to adjust dual pin fixture (60) along an axis perpendicular to the axis defined by passages (223, 330, 430). For example, rocker arm (62) can pivot about connecting pin (63). In view of the teachings herein, other suitable ways and structures to adjust rocker arm (62) will be apparent to those of ordinary skill in the art. By way of example only, rocker arm (62) can be comprised of two pieces that are connected at pin (63) such that each piece of rocker arm (62) could be pivoted independently about an axis defined by pin (63).

In the present example, locking and unlocking locking apparatus (1000) is achieved in about a quarter rotation of disc (400). Furthermore, the sectioned configuration for groove (38) and the stops created by the connection between spheres (413) and circular recesses (38b) of groove (38) are such that in operation rotation of disc (400) is controlled to about a quarter turn in either direction. In other versions more or less rotation of disc (400) may be used to control the locking and unlocking of arch member (200) for rotational adjustment. In view of the teachings herein, other structures, configurations, features, and uses of locking apparatus and its components will be apparent to those of ordinary skill in the art.

III. Exemplary Radial Toothed Arch Member and Connector

FIGS. 29 and 30 illustrate another exemplary arch member (1200) and connector (1300) for use with center insert (100) in a locking apparatus as described above. Arch member (1200) differs from above described arch member (200) in that arch member (1200) includes radially projecting toothed portion (1225) having a plurality of radial teeth (1229) compared to arch member (200) having axially recessed toothed portion (225) having a plurality of teeth (229). Arch member (1200) is configured for use with center insert (100) and dual pin fixture (60) as described above with respect to arch member (200). Therefore the description of those features and structures that make arch member (1200) suitable for use with center insert (100) and dual pin fixture (60) are not repeated here. Instead arch member (1200) is understood to include those respective features and structures as described above with respect to arch member (200). Furthermore, the dimensions and proportions of arch member (1200) and its components (e.g., radially projecting toothed portion (1225)) may vary from that of arch member (200) such that arch member (1200) functions as intended with the other components of locking apparatus (1000).

Connector (1300) differs from above described connector (300) in that connector (1300) includes first engaging member (1340) having a plurality of radial projecting teeth (1341) compared to connector (300) having first engaging member (340) having a plurality of axial projecting teeth (341). Similar to connector (300), in the present example connector (1300) includes second engaging member (1350) having a hexagonal shape In some other versions, second engaging member (1350) can have a shape that is triangular, square, pentagonal, star-shaped or hexalobular, non-circular, or other shapes that will be apparent to one of ordinary skill in the art in view of the teachings herein. Connector (1300) is configured for use with arch member (1200) in a similar fashion as connector (300) is configured for use with arch member (200)

as described above, a difference being that the teeth (1341) of connector (1300) and teeth (1229) of arch member (1200) engage in a radial configuration instead of in an axial configuration as is the case with teeth (341) of connector (300) and teeth (229) of arch member (200). Connector (1300) is configured for use with other components of locking apparatus (1000) in a similar fashion as connector (300) is configured for use with components of locking apparatus (1000) as described above. Therefore, the features and structures that make connector (1300) suitable for use with other components of locking apparatus (1000) are not repeated here. Instead connector (1300) is understood to include those respective features and structures as described above with respect to connector (300). Furthermore, the dimensions and proportions of connector (300) and its components (e.g., first engaging member (1340)) can vary from that of connector (300) such that connector (1300) functions as intended with the other components of locking apparatus (1000). In view of the teachings herein, other structures, features, modifications to, and uses for arch member (1200) (and arch members generally) and connector (1300) (and connectors generally) will be apparent to those of ordinary skill in the art.

In some versions, the components described herein are constructed from biocompatible metals, although not all materials are required to be biocompatible. In some versions such metals are further compatible with MRI and other imaging modalities used in the medical field (e.g., non-magnetic metals such as aluminum or titanium). In some versions the components described herein are constructed from biocompatible plastics, ceramics, carbon or glass fiber reinforced materials, or other polymer-based materials, although again not all materials are required to be biocompatible. In some such versions the components are radiolucent such that they do not appear in certain imaging outputs. In some versions combinations of the above and other materials are used in constructing the various components described above. In view of the teachings herein, other suitable materials of construction for the components described herein will be apparent to those of ordinary skill in the art.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A locking apparatus for use with a patient stabilization device, wherein the locking apparatus comprises:
   a. a fixture configured to retain one or more stabilizing fixtures;
   b. a first member connectable to the fixture, wherein the first member comprises a first toothed portion comprising a first plurality of teeth that project in a circular arrangement around and toward a longitudinal axis defined by the first member;
   c. a second member comprising a second toothed portion comprising a second plurality of teeth that project in a circular arrangement around and away from a longitudinal axis defined by the second member, wherein the second toothed portion selectively engages the first toothed portion of the first member, wherein engagement of the first and second toothed portions secures the rotational position of the first and second members, wherein disengagement of the first and second toothed portions permits adjustment of the rotational position of the first member; and
   d. an actuator connected to the second member, wherein the second member translates in response to rotation of the actuator, wherein translation of the second member moves the second toothed portion of the second member to selectively engage with the first toothed portion of the first member.

2. The apparatus of claim 1, wherein a select one of a the first toothed portion and the second toothed portion comprise a chamfer surface on the plurality of teeth.

3. The apparatus of claim 2, wherein both the first toothed portion and the second toothed portion comprise a chamfer surface on the plurality of teeth.

4. The apparatus of claim 3, wherein at an initial point of engagement between the first member and the second member, the chamfer surface on the plurality of teeth of the first toothed portion engages with the chamfer surface on the plurality of teeth of the second toothed portion.

5. The apparatus of claim 1, further comprising an arm, wherein the arm comprises an opening, wherein the opening is configured to receive an engaging portion of the second member.

6. The apparatus of claim 5, wherein the engaging member comprises a non-circular shape, wherein the opening of the arm comprises a complementary non-circular shape.

7. The apparatus of claim 6, wherein the engaging member comprises a hexagonal shape, wherein the opening of the arm comprises a complementary hexagonal shape.

8. The apparatus of claim 1, wherein the one or more stabilizing fixtures comprise one or more skull pins.

9. The apparatus of claim 1, wherein disengagement of the first and second toothed portions permits adjustment of the rotational position of the first member while restricting rotation of the second member.

10. A locking apparatus for use with a patient stabilization device, wherein the locking apparatus comprises:
    a. an arch member comprising:
       i. a first toothed portion, and
       ii. a first passage extending longitudinally through the arch member;
    b. a connector comprising:
       i. a first engaging member, wherein the first engaging member is configured to selectively engage the first toothed portion of the arch member,
       ii. a second engaging member, and
       iii. a second passage extending longitudinally through the connector;
    c. an opening, wherein the opening is configured to receive the second engaging member of the connector;
    d. a bolt comprising a shaft, wherein the shaft extends through the second passage of the connector and within the first passage of the arch member; and
    e. an insert, wherein the insert is configured to be received within the first passage of the arch member.

11. The apparatus of claim 10, wherein the first passage comprises a first interior threaded portion and a second interior threaded portion.

12. The apparatus of claim 11, wherein the shaft of the bolt comprises a split end comprising a threaded outer surface, wherein the split end defines a void space, wherein the threaded outer surface of the split end threadably connects with the second interior threaded portion of the first passage of the arch member.

13. The apparatus of claim 12, wherein the insert comprises a threaded collar and a tapered portion, wherein the threaded collar threadably connects with the first interior threaded portion of the first passage of the arch member, wherein the tapered portion of the insert is insertable within the void space of the split end of the bolt.

14. The apparatus of claim 13, wherein insertion of the tapered portion of the insert within the void space of the split end of the bolt forces the split end of the bolt to flex outwardly against the second interior threaded portion of the first passage of the arch member.

15. The apparatus of claim 14, wherein the arch member and the bolt are configured to adjustably rotate in unison when the connector is not engaged with the arch member.

16. The apparatus of claim 15, wherein the connector is restricted from rotation and is permitted to translate to achieve selective engagement with the arch member.

17. The apparatus of claim 16, wherein the second engaging member of the connector comprises a non-circular shape, wherein the opening comprises a complementary non-circular shape.

18. The apparatus of claim 17, wherein the second engaging member of the connector comprises a hexagon shape.

19. The apparatus of claim 10, wherein the first engaging member of the connector comprises a second toothed portion.

20. A head fixation device comprising a locking apparatus, wherein the locking apparatus comprises:
 a. a first member positioned between a pin fixture and an arm of the head fixation device;
 b. a second member positioned between the first member and an arm of the head fixation device, wherein the rotational position of the first member relative to the second member is selectively locked by selective engagement between the first member and the second member;
 c. a first starburst feature connected with a select one of the first member and the second member, wherein the first starburst feature is recessed within the select one of the first member and the second member, wherein the starburst feature comprises a plurality of teeth in a circular arrangement and that project toward a longitudinal axis defined by the select one of the first member and the second member; and
 d. a second starburst feature connected with a select one of the first member and the second member, wherein the second starburst feature comprises a plurality of teeth in a circular arrangement and that project away from a longitudinal axis defined by the select one of the first member and the second member.

* * * * *